(12) United States Patent
Eberle

(10) Patent No.: US 6,254,969 B1
(45) Date of Patent: Jul. 3, 2001

(54) SHELF LIFE INDICATOR

(75) Inventor: Theodore F. Eberle, Chicago, IL (US)

(73) Assignee: Crown Cork & Seal Technologies Corporation, Alsip, IL (US)

( * ) Notice: Subject to any disclaimer, the term of this patent is extended or adjusted under 35 U.S.C. 154(b) by 0 days.

(21) Appl. No.: 09/205,430

(22) Filed: Dec. 4, 1998

Related U.S. Application Data

(60) Provisional application No. 60/067,311, filed on Dec. 5, 1997, now abandoned.

(51) Int. Cl.[7] ............................... B32B 27/14; B32B 3/00
(52) U.S. Cl. ........................ 428/195; 428/206; 428/207; 428/474.4
(58) Field of Search ..................................... 428/195, 206, 428/207, 474.4

(56) References Cited

U.S. PATENT DOCUMENTS

| | | | |
|---|---|---|---|
| 4,382,700 | * 5/1983 | Youngren | 374/102 |
| 4,526,752 | * 7/1985 | Perlman et al. | 422/56 |
| 4,629,330 | * 12/1986 | Nichols | 368/89 |
| 5,021,515 | 6/1991 | Cochran et al. | 525/371 |
| 5,053,339 | * 10/1991 | Patel | 436/2 |
| 5,633,836 | * 5/1997 | Langer et al. | 368/327 |
| 5,639,815 | 6/1997 | Cochran et al. | 524/413 |

FOREIGN PATENT DOCUMENTS

| | | |
|---|---|---|
| WO 89/01012 | 2/1989 | (WO) . |
| WO 95/11801 | 4/1995 | (WO) . |
| WO 96/29362 | 9/1996 | (WO) . |

* cited by examiner

Primary Examiner—William Krynski
Assistant Examiner—B. Shewareged
(74) Attorney, Agent, or Firm—Woodcock Washburn Kurtz Mackiewicz & Norris LLP

(57) ABSTRACT

A shelf life indicating structure including a substrate printed with an oxygen sensitive ink in combination with an oxygen scavenging layer is disclosed. The oxygen scavenging layer prevents oxygen reaching the substrate for a predetermined interval. Once the finite oxygen scavenging capability of the layer is exhausted, oxygen reaches the substrate, thereby activating a visible indication such as a color change, in the ink. The substrate and layer may be formed into a patch or label for a package, and covered with an oxygen impermeable layer, such as a strip of aluminum foil which can be peeled off to initiate a shelf life indication structure. A method associated with the shelf life indicating structure is also provided.

26 Claims, 1 Drawing Sheet

SHELF LIFE INDICATOR

This application claims section 119(e) priority based on provisional application 60/067,311, filed Dec. 5, 1997, abandoned.

FIELD OF THE INVENTION

This invention relates to shelf life indicating structures and in particular to structures for indicating the shelf life of a product within a package.

BACKGROUND

Shelf life or freshness indicators affixed to food, beverage, and other product packages are useful and beneficial to producers and the public. A common way of indicating the shelf life of a product is to print a "sell by" or "use by" date on the package containing the product. A disadvantage of this type of pre-calculated, shelf life indicator is that it takes no account of the actual conditions (temperature, humidity, etc) under which the product is stored. Further, the pre-calculated, printed shelf life indicator may be easily visually lost in circumstances in which a consumer merely glances at the product, especially if the packaging contains other eye-catching text and graphics.

It is an object of the present invention to provide an "active" indicator, which is also more readily visible to the user, and which more precisely reflects the effects of varying storage conditions.

SUMMARY

Accordingly there is provided a structure for giving a shelf life indication with respect to a product, the structure comprising a first layer including an oxygen sensitive ink which gives a visible indication when exposed to a predetermined minimum quantity of oxygen, and a second layer including an oxygen scavenging material adapted to try and prevent oxygen reaching the oxygen sensitive ink for a predetermined interval, the oxygen scavenging material having a finite scavenging capability such that after the predetermined interval the oxygen scavenging material is unable to prevent oxygen reaching the oxygen sensitive ink, causing the ink to react with the oxygen to give its visible indication so as to provide a shelf life indication.

Thus the shelf life indicator is activated by the actual amount of oxygen to which the package is exposed. When the oxygen scavenging capabilities of the scavenging layer have been exhausted, the indicator will be triggered. Conveniently the visible indication given by the oxygen sensitive ink is a change in color from a first color to a second color when exposed to the predetermined quantity of oxygen. This will also include a change from clear to colored, making the ink visible to the user for the first time. Examples of synthetic oxygen sensitive inks include those based on ferrocene or pyrogallol components, thiazine dyes or other oxygen sensing dyes, whilst naturally occurring substances such as enzymes found in foodstuffs may conceivably also be employed. Examples of oxygen scavenging materials include those described in WO 89/01012, WO 95/11801, and WO 96/29362, although other materials have been proposed.

Preferably there is also provided means for initiating the shelf life indication structure. Conveniently the structure includes an additional oxygen impermeable layer which is removable in order to initiate the shelf life indication structure. Conveniently the oxygen impermeable layer is also impermeable to light, and the oxygen scavenging layer may be photo-initiated, for example by the user removing the impermeable layer and holding the structure to the light for a predetermined time. The impermeable layer is typically a layer of metallic foil, such as aluminum foil. Conveniently the shelf life indicating structure is in the form of a label attached to a package.

The invention further resides in a method of indicating the shelf life of a product comprising the steps of:
  a) providing a first substrate layer including or imprinted with an oxygen sensitive ink adapted to give a visible indication when exposed to a predetermined minimum quantity of oxygen,
  b) covering the first layer with a second layer including an oxygen scavenging material adapted to prevent oxygen reaching the oxygen scavenging ink for a predetermined interval,
  c) covering both first and second layers with a removable layer of oxygen impermeable material,
  d) forming the first, second and third layers into a patch or label, and
  e) attaching the patch or label to the package to provide a shelf life indication system.

DESCRIPTION OF A PREFERRED EMBODIMENT

Figure 1:
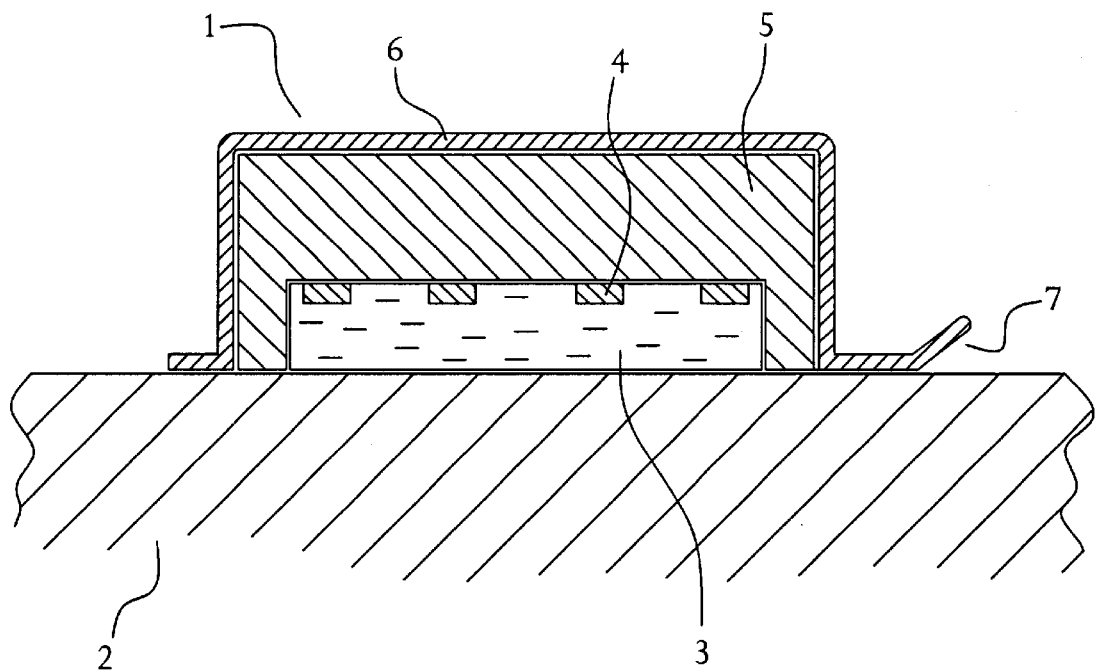
FIG. 1 is a cross sectional view of an embodiment of the present invention.

The invention will now be further described, by way of example only, with reference to the attached figure which is a sectional view of a shelf life indicating structure in accordance with the present invention.

Referring to the figure, a patch is shown generally at 1 (in exaggerated form to aid with clarity), attached to a product 2 such as for example an air freshener. The patch comprises a base substrate 3 printed with an oxygen sensitive ink shown generally at 4. The ink may include, for example, a ferrocene compound (which changes color from yellow to green on contact with oxygen), or pyrogallol (which changes from clear to brown). The printing may typically be a logo or even a message. Clearly, the printing of the oxygen sensitive ink must be carried out in an inert atmosphere, unless the ink can be "initiated" to activate the oxygen sensitivity after printing.

The printed base substrate 3 is immediately laminated to a layer 5 of oxygen scavenging material. It is important to note that the oxygen scavenging material may be an oxidizable organic component, which may be an oxidizable polymer. The use of an oxidizable polymer as the oxidizable organic component has the advantage, broadly speaking, over the use of an oxidizable non-polymeric component in that it is less likely to affect adversely the properties of a non-oxidizable polymer with which it is blended (if any). Also, it is possible for two or more polymers, two or more oxidizable organic components, or two or more catalysts to be used. It is possible also for a metal catalyst to be used in combination with a non-metal catalyst. For example, with some oxidizable organic components an organic peroxide may be used in combination with the metal catalyst.

Specifically, the oxygen scavenging material can be a polymer such as that described in WO 89/01012 including an oxidizable polymer such as polypropylene, polyethylene, PET, or a mixture of one of these together with a nylon, together with a transition metal catalyst such as cobalt.

The composition of the oxygen scavenging material may comprise a polymer, an oxidizable organic component, and a metal catalyst for the oxidation of the oxidizable organic component. The information provided below regarding specific chemical compositions that may be employed by the present invention is generally provided in WO 89/01012. The compositions and developments disclosed in WO 95/11801 and WO 96/29362, and incorporated herein by reference, may also be employed by the present invention. The development of oxygen scavenging science and materials is progressing, and the materials recited herein may be replaced by recent products of the ongoing development. Further, the compositions of materials that may be employed with the present invention may be tailored to the particular application. Specifically, the oxygen scavenging capacity (based on material composition, thickness, and like parameters that will be apparent to persons familiar with such technology and parameters) may be chosen according to the shelf life of the product.

The term "catalyst," as used in the specification and appended claims, is used as it is generally understood in the art, but not necessarily to imply that it is not consumed at all in the oxidation. It is indeed possible that the catalyst may be converted cyclically from one state to another and back again as successive quantities of the oxidizable component is consumed by successive quantities of oxygen. However, it may be that some is lost in side reactions, possibly contributing directly to oxygen-scavenging, or that the "catalyst" is more properly described as an initiator (for example, generating free radicals which through branching chain reactions lead to the scavenging of oxygen out of proportion to the quantity of "catalyst").

The oxidizable component/metal catalyst combination in all aspects my be selected by experimental trial and error such as a person skilled in the art may readily devise. A good preliminary screening can be achieved by means of pure scavenging measurements on granules (a possible procedure is shown in Example 7 of publication WO 89/01012). A metal catalyst that is highly effective for one oxidizable organic component may be less effective for another. The effectiveness may depend on the precise grade of the organic component or on the polymer in the composition.

The role that the metal catalyst plays is not fully understood, although we regard metals with at least two positive oxidation states, especially transition metals, as the most promising catalysts when added in one of the positive oxidation states, particularly as cations. Thus, cobalt added in the II and III state, rhodium added in the II state, and copper added in the II state have proven effective with some oxidizable organic components. Addition in the form of a carboxylate has proven convenient. Generally speaking, higher levels of catalysts achieve better scavenging. In the absence of undesired interactions between the catalyst and the other components (such as depolymerization) a weight fraction of metal relative to the total composition of up to 5,000 ppm can be readily contemplated. Levels of at least 10, preferably 50, more preferably 100 ppm of metal can achieve catalysis (the precise level being determined by trial and error for a particular overall composition).

Higher weight fractions of the oxidizable components may be especially valuable for the present invention. Particularly interesting oxidizable polymers are the polyamides, especially those containing groups of the formula -arylene-$CH_2$—NH—CO—, conveniently in —NH—$CH_2$-arylene-$CH_2$—NH—CO-alkylene-CO— units. These polyamides are of especial interest with cobalt and rhodium catalysts. Especially suitable arylene groups are phenylene groups, particularly m-phenylene groups, which may be alkyl-substituted and/or condensed with other un-substituted or alkyl-substituted aromatic rings. Alkylene and alkyl groups conveniently have from 1 to 10 carbon atoms and my be straight-chain or branched. Especially suitable alkylene groups are n-butylene groups. MXD6 is very suitable. Conveniently, the relative viscosity (also called viscosity ratio) of polyamides containing—NH—$CH_2$-arylene-$CH_2$—NH—CO-alkylene-CO— groups lies in the range from 1.5 to 4.5, especially 2.0 to 3.6 (measured for solutions in 95% aqueous sulphuric acid containing 1 g of polymer per 100 $cm^3$ solution).

Fully aliphatic polyamides are promising, comprising —CO($CH_2$)n CONH($CH_2$)m NH— or —($CH_2$)pCONH— units (n, m, and p being integers usually 4, 5, or 6), although we have so far not achieved the very good results which we have achieved with MXD6. In general, the polyamide may include polymer linkages, side-chains, and end groups not related to the formal precursors of a simple polyamide (i.e. compounds having at least two amino groups per molecule together with those having at least two carboxylic acid groups per molecule, or aminocarboxylic acids). Conveniently, at least 90 mole percent of the polymer's formal precursors will be such. However, a polymer including a minority of amide linkages would in principle work, such a polymer perhaps being used as the sole polymeric component of the composition. Even in such a case, however, one would expect to include in the composition a concentration of —CONH— linkages similar to that which one would use with MXD6—i.e. concentrations of —CONH— in the total composition of at least 0.08 mmol/g, most commonly up to 0.6 mmol/g.

From a purely chemical standpoint, non-polymeric amides are attractive as oxidizable organic components. Non-polymeric compounds containing a group or groups of the formula -alkylene-CO—NH—$CH_2$-1,3-phenylene-$CH_2$—NH—CO-alkylene- are of interest, especially with cobalt and rhodium catalysts. The above comments on alkylene and 1,3-phenylene groups, made with references to polymeric amides, apply here except that n-butylene is not so convenient if an alkylene group is terminated by H. An example of such a non-polymeric compound is n—$C_3H_7$—CO—NH—$CH_2$—m—$C_6H_4$—$CH_2$—NH—CO—n—$C_3H_7$, which in the presence of cobalt we have found to scavenge oxygen well, although its suitability for use in accordance with the present invention needs of course to be determined by trial and error in a particular application.

Other non-polymeric oxidizable compounds are also of interest, for instance conventional antioxidants including substituted phenols, especially 2,4,6-tri-(t-butyl) phenol.

Subject to the above preferences on physical properties, non-oxidizable polymers used according to the present invention in all its aspects can be chosen with fair freedom, unless there is some specific inhibition of the scavenging system or other untoward interaction. In principle, there may be a favorable interaction (e.g. if the non-oxidizable polymer contains as catalyst residues metals catalyzing the oxidation of the oxidizable organic component); but in current commercial products the levels are usually low and the catalyst may be at least partially poisoned by the other residues or additives.

Polymers (formally) of one or more phthalic acids with one or more organic compounds containing at least two alcoholic hydroxy groups per molecule can offer fair impermeability in the absence of scavenging. Preferably, the permeabilities should be less than 6.0 cm3 mm/(m2 atm day). Phthalic acid polyesters based on terephthalic or isophthalic acid are commercially available and convenient; the hydroxy compounds are typically ethylene glycol (which may yield diethylene glycol units in situ), and 1,4,-di-(hydroxymethyl)-cyclohexane. Conveniently, the intrinsic viscosity (also called limited viscosity number) for a phthalic acid polyester lies in the range from 0.6 to 1.2, especially 0.7 to 1.0 (for o-chlorophenol solvent). 0.6 corresponds approximately to a viscosity average molecular weight of 59 000, and 1.2 to 112 000.

In general, the phthalate polyester may include polymer linkages, side chains, and end groups not related to the formal precursors of a simple phthalate polyester previously specified. Conveniently, at least 90 mole percent will be terephthalic acid and at least 45 mole percent an aliphatic glycol or glycols, especially ethylene glycol.

Polyolefins blended with a scavenging system have been found to work, and by lamination or coating with less permeable material walls or layers of interesting overall barrier properties should be achievable.

The composition may, as previously mentioned, include other components such as pigments, fillers, and dyestuffs. Usually, the total quantity of such components will be less than 10%, more usually less than 5%, by weight relative to the whole composition.

Compositions which we think may be of especial importance include the following (the percentages being the weight fractions relative to the total composition):

compositions comprising at least 90%, preferably 95%, of polyethylene terephthalate and/or a polyamide taken together and having a permeability to oxygen of not more than 0.01 cm3 mm/(m2 atm day);

compositions containing at least 90% of polyethylene terephthalate, preferably 95%, and having a permeability to oxygen of not more than 0.3 cm3 mm/m2 atm day), and preferably not more than 0.1 cm3 mm/(m2 atm day), and more preferably not more 0.03 cm3 mm/(m2 atm day), preferably at least 0.5%, more preferably 1%, and also preferably less than 7% of the composition consisting of a polyamide; and compositions comprising at least 90%, preferably 95%, of a polyamide and having a permeability to oxygen of not more than 0.01 cm3 mm/(m2 atm day).

The composition is preferably formed by mixing the metal catalyst with the other component or components of the composition all together or in any sequence. The metal catalyst is preferably added in the form of a solution or slurry. Conveniently, the mixing includes or is followed by melt-blending at a temperature appropriate to the components, commonly in the range from 100° C. to 300° C. We have found additions of catalyst in the range of 10 to 250, especially 50 to 200, ppm to be convenient.

The oxidation catalyst may be added to the monomers from which one or more polymeric components of a composition are made, rather than being added as proposed above in a subsequent blending step. Clearly, if the oxidation catalyst neither interfaces with nor is affected by the polymerization process than this may be an attractive option. If the catalyst interfaces or assists with the polymerization or is at least partially poisoned by the usual steps in the polymerization (as may be the case with cobalt and polyethylene terephthalate production), then modification or careful selection of polymerization protocols will be necessary.

In some systems at least, the scavenging properties do not emerge immediately after the blending, but only after ageing. This may be because catalyst species have to migrate to relevant sites in the composition because it is incorporated so as to be present in the "wrong" phase or because the relevant sites in the oxidizable component to which they were attached during processing were very largely oxidized during processing, or because a slow initiation is involved, or for some other reason. Prolonged ageing at ordinary temperatures, or ageing accelerated by elevated temperatures, are in principle possible but are costly. However, the higher the level of catalyst used, generally the less ageing is required.

The layer 5 is transparent to allow the substrate 3 to be viewed therethrough. The substrate 3 and the oxygen scavenging layer 5 are together covered by a strip of aluminum foil 6, which is provided with a pull tab 7 to enable the foil to be peeled off when required.

In use the foil layer 6 is removed to initiate the structure. This may be done at the end of the manufacturing or packing process, at the point of sale, or by the purchaser of the product, depending on the circumstances. The removal of the foil allows oxygen to reach the layer 5, where it is absorbed by the oxygen scavenging material. The removal of the foil layer 6 will also allow light to reach the oxygen scavenging layer 5, which can be used to photo-initiate the oxygen scavenging properties of the layer 5, for example by the user removing the foil 6 and holding the package with the patch exposed to the light for at least a certain period. The oxygen scavenging layer will have a finite, predetermined oxygen scavenging capability, which can be changed by varying either the concentration of the components within the layer, or the thickness of the layer itself. After a predetermined time, the oxygen scavenging capability of the layer 5 will be exhausted, and oxygen will start to reach the base substrate 3. This will activate the oxygen sensitive ink 4, changing its color, and giving a visible indication which can be clearly seen through the transparent layer 5.

For some composition of materials, the oxygen-scavenging effect can be suppressed by cooling the composition. In other words, the oxygen scavenging effect may be temperature dependent. Further, the oxygen scavenging effect may depend upon illumination. Therefore, as explained more fully in Publication WO 89/01012, the permeance and permeability of oxygen scavenging layer 5 (assuming a particular composition of, for example, a catalyst and polymer, as well as a particular thickness of layer 5) may depend on time, temperature, and degree of exposure to light and oxygen content or partial pressure of the atmosphere. As will be understood by persons familiar with oxygen scavenging materials in light of the present disclosure, the patch 1 (and particularly the layer 5) may be engineered to provide an indication of overall freshness of the product 2. Specifically, the thickness and composition of the materials comprising patch I may be chosen (according to the principles provided in the present disclosure, including the information that is incorporated by reference) such that the exhaustion of the oxygen scavenging capability of layer 5, based on the time, temperature, light and oxygen conditions of exposure, matches the degradation of freshness of product 2. For example, if the rate at which a particular air freshener becomes stale is highly dependent on temperature, the materials and thickness of layer 5 may be chosen such that the rate of exhaustion of its oxygen scavenging capability is similarly dependent on temperature.

It will be appreciated that a variety of different inks and oxygen scavenging systems can be employed within the general scope of the present invention. Furthermore, although the invention has been described with reference to a shelf life indicator, for example how to indicate when an air freshener has ceased to be effective, it will be appreciated that other uses may be readily envisaged. These will include other shelf life activities such as spoilage of foodstuffs and beverages, and the recommended useful life of pharmaceuticals and health and beauty products such as lipsticks, eye drops etc. Other opportunities such as delayed promotional messages, or other prize or gaming schemes could be envisaged. Whilst such activities are not strictly shelf life indications, they are to be considered within the scope of the present invention.

What is claimed is:

1. A shelf life indicator for indicating shelf life of a product, the indicator comprising:
a structural first layer including an oxygen sensitive ink for providing a visible indication when exposed to a predetermined minimum quantity of oxygen,
a second layer including an oxygen scavenging material that prevents oxygen from reaching the oxygen sensitive ink while the oxygen scavenging capability of the oxygen scavenging material is substantially not exhausted, the second layer becoming unable to prevent the predetermined quantity of oxygen from reaching the ink after the oxygen scavenging material is substantially exhausted, and
a removable, metallic foil, oxygen-impermeable layer, whereby removal of the oxygen-impermeable layer may initiate the shelf life indicator,
whereby the ink provides the visible indication substantially after the oxygen scavenging capability is substantially exhausted to provide a shelf life indication.

2. The shelf life indicator of claim 1 wherein the oxygen scavenging material has a finite scavenging capability that is substantially exhausted after a predetermined interval.

3. The shelf life indicator of claim 2 wherein the predetermined interval may be predetermined based on parameters comprising temperature, oxygen content of the atmosphere, and composition of the oxygen scavenging material.

4. The shelf life indicator according to claim 1, wherein the visible indication given by the oxygen sensitive ink is a change in color from a first color to a second color.

5. The shelf life indicator according to claim 1, wherein the visible indication given by the oxygen sensitive ink is a change from transparent to visible.

6. The shelf life indicator according to claim 1, wherein the oxygen scavenging material comprises an oxidizable polymer.

7. The shelf life indicator according to claim 6, wherein the oxygen scavenging material includes a transition metal catalyst.

8. The shelf life indicator according to claim 7 wherein the catalyst is cobalt.

9. The shelf life indicator according to claim 7 wherein the oxygen scavenging material includes a non-oxidizable component mixed with the oxygen scavenging material and the catalyst.

10. The shelf life indicator according to claim 9 wherein the oxidizable polymer includes a polyamide including groups of the formula -arylene-CH2—NH—CO—.

11. A shelf life indicator for indicating shelf life of a product, the indicator comprising:
a structural first layer including an oxygen sensitive ink for providing a visible indication when exposed to a predetermined minimum quantity of oxygen, and
a second layer including an oxygen scavenging material that prevents oxygen from reaching the oxygen sensitive ink while the oxygen scavenging capability of the oxygen scavenging material is substantially not exhausted, the second layer becoming unable to prevent the predetermined quantity of oxygen from reaching the ink after the oxygen scavenging material is substantially exhausted,
whereby the ink provides the visible indication substantially after the oxygen scavenging capability is substantially exhausted to provide a shelf life indication.

12. A shelf life indicator for indicating shelf life of a product, the indicator comprising:
a structural first layer including an oxygen sensitive ink for providing a visible indication when exposed to a predetermined minimum quantity of oxygen,
a second layer including an oxygen scavenging material that prevents oxygen from reaching the oxygen sensitive ink while the oxygen scavenging capability of the oxygen scavenging material is substantially not exhausted, the second layer becoming unable to prevent the predetermined quantity of oxygen from reaching the ink after the oxygen scavenging material is substantially exhausted, and
a removable light-impermeable layer, whereby removal of the light-impermeable layer may initiate the shelf life indicator,
whereby the ink provides the visible indication substantially after the oxygen scavenging capability is substantially exhausted to provide a shelf life indication.

13. The shelf life indicator according to claim 1, further comprising a removable oxygen-impermeable layer disposed substantially over the second layer, whereby removal of the oxygen-impermeable layer may initiate the shelf life indicator.

14. The shelf life indicator according to claim 13, wherein the shelf life indicator forms a label attached to a package.

15. A combination of a package and a shelf life indicator comprising a first layer including an oxygen sensitive ink for providing a visible indication when exposed to a predetermined minimum quantity of oxygen, and a second layer including an oxygen scavenging material adapted to prevent oxygen from reaching the oxygen sensitive ink for a predetermined interval, the oxygen scavenging material having a finite scavenging capability such that after the predetermined interval the oxygen scavenging material is unable to prevent oxygen from reaching the oxygen sensitive ink, whereby the ink provides the visible indication substantially after the predetermined interval to provide a shelf life indication.

16. The shelf life indicator of claim 10 wherein the polymer includes a polyamide including groups of the formula —NH—CH2-arylene-CH2—NH—CO-alkylene-CO—.

17. The shelf life indicator according to claim 12, wherein the oxygen scavenging material comprises an oxidizable polymer.

18. The shelf life indicator according to claim 17, wherein the oxygen scavenging material includes a transition metal catalyst.

19. The shelf life indicator according to claim 18 wherein the catalyst is cobalt.

20. The shelf life indicator according to claim 18 wherein the oxygen scavenging material includes a non-oxidizable component mixed with the oxygen scavenging material and the catalyst.

21. The shelf life indicator according to claim 20 wherein the oxidizable polymer includes a polyamide including groups of the formula -arylene-CH2—NH—CO—.

22. The shelf life indicator of claim 21 wherein the oxidizable polymer includes a polyamide including groups of the formula —NH—CH2-arylene-CH2—NH—CO-alkylene-CO—.

23. A shelf life indicator for indicating shelf life of a product, the indicator comprising:
a patch including at least a first layer and a second layer, the first layer including a substrate and an oxygen sensitive ink therein for providing a visible indication when exposed to a predetermined minimum quantity of oxygen, and
the second layer including an oxygen scavenging material that prevents oxygen from reaching the oxygen sensitive ink while the oxygen scavenging capability of the oxygen scavenging material is substantially not exhausted, the second layer becoming unable to prevent the predetermined quantity of oxygen from reaching the ink after the oxygen scavenging material is substantially exhausted, and
whereby the ink provides the visible indication substantially after the oxygen scavenging capability is substantially exhausted to provide a shelf life indication.

24. The shelf life indicator of claim 23 wherein the patch further includes a third layer that comprises a removable oxygen-impermeable layer, whereby removal of the oxygen-impermeable layer may initiate the shelf life indicator.

25. A shelf life indicator for indicating shelf life of a product, the indicator comprising:
a first layer indicating a substrate and an oxygen sensitive ink therein for providing a visible indication when exposed to a predetermined minimum quantity of oxygen, and
a second layer including an oxygen scavenging material that prevents oxygen from reaching the oxygen sensitive ink while the oxygen scavenging capability of the oxygen scavenging material is substantially not exhausted, the second layer becoming unable to prevent the predetermined quantity of oxygen from reaching the ink after the oxygen scavenging material is substantially exhausted, the second layer being laminated on the first layer,
whereby the ink provides the visible indication substantially after the oxygen scavenging capability is substantially exhausted to provide a shelf life indication.

26. The shelf life indicator of claim 25 wherein the indicator further includes a third layer that comprises a removable oxygen-impermeable layer, the third layer being disposed over the second layer and in contact therewith to form a patch or a label, whereby removal of the oxygen-impermeable layer may initiate the shelf life indicator.

* * * * *